US012673922B1

(12) United States Patent
Aldabayan et al.

(10) Patent No.: US 12,673,922 B1
(45) Date of Patent: Jul. 7, 2026

(54) 5-(3-BROMOPHENYL)-3-((DIETHYLAMINO)METHYL)-5-METHYLIMIDAZOLIDINE-2,4-DIONEAS

(71) Applicant: KING FAISAL UNIVERSITY, Al-Ahsa (SA)

(72) Inventors: Yousef Saad Yousef Aldabayan, Al-Ahsa (SA); Hany Mohamed Abd El-Lateef Ahmed, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 19/395,521

(22) Filed: Nov. 20, 2025

(51) Int. Cl.
*C07D 233/76* (2006.01)
*A61K 31/417* (2006.01)
*A61P 31/04* (2006.01)

(52) U.S. Cl.
CPC .......... *C07D 233/76* (2013.01); *A61K 31/417* (2013.01); *A61P 31/04* (2018.01)

(58) Field of Classification Search
CPC ...... C07D 233/76; A61P 31/04; A61K 31/417
See application file for complete search history.

(56) References Cited

U.S. PATENT DOCUMENTS

| | | | | |
|---|---|---|---|---|
| 8,168,666 | B2 | 5/2012 | Matsuda et al. | |
| 2012/0214806 | A1 * | 8/2012 | Andreini | A61P 3/00 544/98 |
| 2012/0238609 | A1 * | 9/2012 | Srivastava | A61K 31/4188 514/389 |
| 2014/0296575 | A1 | 10/2014 | Ma et al. | |

FOREIGN PATENT DOCUMENTS

WO WO-2018053199 A1 * 3/2018 ............. G06T 7/001

OTHER PUBLICATIONS

Rai et al.(Year: 2019).*
Mistry (Year: 2012).*
Mohamed, et al. “Synthesis of Imidazolidine-2,4-dione and 2-thioxoimidazolidin-4-one Derivatives as Inhibitors of 1 Virulence Factors Production in Pseudomonas aeruginosa.” Archiv der Pharmazie, vol. 353, No. 5, May 2020, e1900352. Wiley Online Library, https://doi.org/10.1002/ardp.201900352. (Abstract).

* cited by examiner

*Primary Examiner* — Jeffrey S Lundgren
*Assistant Examiner* — Ibrahim D Bori
(74) *Attorney, Agent, or Firm* — Nath, Goldberg & Meyer; Joshua B. Goldberg

(57) ABSTRACT

A compound 5-(3-bromophenyl)-3-((diethylamino)methyl)-5-methylimidazolidine-2,4-dione, its synthesis, use as an antibacterial agent and an inhibitor of Chronic Obstructive Pulmonary Disease (COPD).

6 Claims, 2 Drawing Sheets

5-(3-BROMOPHENYL)-3-((DIETHYLAMINO)METHYL)-5-METHYLIMIDAZOLIDINE-2,4-DIONEAS

BACKGROUND

1. Field

The present disclosure relates to the compound 5-(3-bromophenyl)-3-((diethylamino)methyl)-5-methylimidazolidine-2,4-dioneas, its synthesis, and its use as an antibacterial and/or chronic obstructive pulmonary disease (COPD) inhibition agent.

2. Description of the Related Art

In recent years, most pathogenic bacteria have developed resistance to commonly used antibiotics and anti-infective medicines. Furthermore, in bacterial consortiums, cross-resistances have emerged in MDR (multidrugresistant) microorganisms. As such, continuing antimicrobial agent investigations are critical and should always be up to date.

Heterocyclic chemistry plays a pivotal role in drug discovery, serving as the foundation for many pharmacologically active compounds. In recent years, the exploration of privileged organic scaffolds has emerged as a key focus in medicinal chemistry, driving the development of novel therapeutic agents Derivatives of hydantoin have found practical applications in various fields such as antiandrogenic, antihypertensive, antibacterial, anti-mutagenic agent, antiviral, antioxidant, antimutagenic, anticancer, antimicrobial, antiparasitic, antifungal, anti-HIV, anticonvulsant, antidiabetic, and antiinflammatory activities. Moreover, hydantoin derivatives have application as agrochemicals (bactericides herbicidal and fungicidal) and developing of dyes. Pharmacological studies have shown that these molecules are effective against various strains of microorganisms. In addition, Mannich bases exhibit a broad spectrum of biological activities, including anticonvulsant, antimalarial, antiviral, antifungal, and antibacterial properties. Additionally, they demonstrate analgesic, anti-inflammatory, anticancer, and various other pharmacological effects, making them valuable in medicinal chemistry and drug development. Also, Mannich bases are widely utilized in various industrial and commercial applications. They play a significant role in treating natural macromolecular materials, including leather, paper, and textiles. Additionally, they are essential in synthetic polymer production, petroleum industry additives, and water treatment processes. Beyond these uses, Mannich bases serve as analytical reagents, cosmetic ingredients, and dye components, showcasing their versatility across multiple sectors. From both environmental and economic perspectives, traditional chemical synthesis methods are increasingly recognized as unsustainable and in need of replacement. Multicomponent coupling reactions (MCRs) offer a promising solution, being more cost-effective, efficient, and less wasteful.

Therefore, there is a critical need to create new antimicrobial and antibacterial agents with potent anti-drug-resistant microorganism activity.

SUMMARY

The present subject matter relates to a novel heterocyclic compound. The compound 5-(3-bromophenyl)-3-((diethylamino)methyl)-5-methylimidazolidine-2,4-dione (4) can be synthesized via a one-pot three-component reaction of 5-(3-bromophenyl)-5-methylimidazolidine-2,4-dione (1), formaldehyde 2, and diethylamine 3 in ethanol. The synthesized compound 4 can exhibit strong antibacterial activity. For example, the compound 4 can exhibit stronger antibacterial activity than the standard drug ciprofloxacin against *Bacillus cereus* and *Escherichia coli* at varying concentrations (10,000 ppm, 30,000 ppm, and 40,000 ppm). The compound can be an effective antibiotic as well as an inhibitor of key inflammatory pathways associated with Chronic Obstructive Pulmonary Disease (COPD). Compound 4 showed notable inhibition of pro-inflammatory cytokines (e.g., TNF-α, IL-6) and reactive oxygen species (ROS) production in lung epithelial cells, suggesting a dual-function profile as both an antibacterial and an anti-COPD agent.

In an embodiment, the present subject matter relates to a 5-(3-bromophenyl)-3-((diethylamino)methyl)-5-methylimidazolidine-2,4-dione compound having the formula I:

I

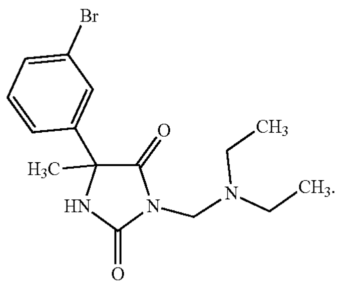

In another embodiment, the present subject matter relates to a pharmaceutically acceptable composition comprising a therapeutically effective amount of the 5-(3-bromophenyl)-3-((diethylamino)methyl)-5-methylimidazolidine-2,4-dione compound and a pharmaceutically acceptable carrier.

In a further embodiment, the present subject matter relates to a method of treating a bacterial infection in a patient comprising administering to a patient in need thereof a therapeutically effective amount of the 5-(3-bromophenyl)-3-((diethylamino)methyl)-5-methylimidazolidine-2,4-dione compound.

In one more embodiment, the present subject matter relates to a method of making the 5-(3-bromophenyl)-3-((diethylamino)methyl)-5-methylimidazolidine-2,4-dione compound, the method comprising: stirring 5-(3-bromophenyl)-5-methylimidazolidine-2,4-dione and formaldehyde in ethanol to form a first mixture; adding diethylamine to the first mixture to obtain a second mixture; stirring the second mixture with reflux; cooling the second mixture to form a solid; and filtering the solid and recrystallizing from ethanol to obtain the 5-(3-bromophenyl)-3-((diethylamino)methyl)-5-methylimidazolidine-2,4-dione compound.

These and other features of the present subject matter will become readily apparent upon further review of the following specification.

DETAILED DESCRIPTION OF THE PREFERRED EMBODIMENTS

Figure 1:
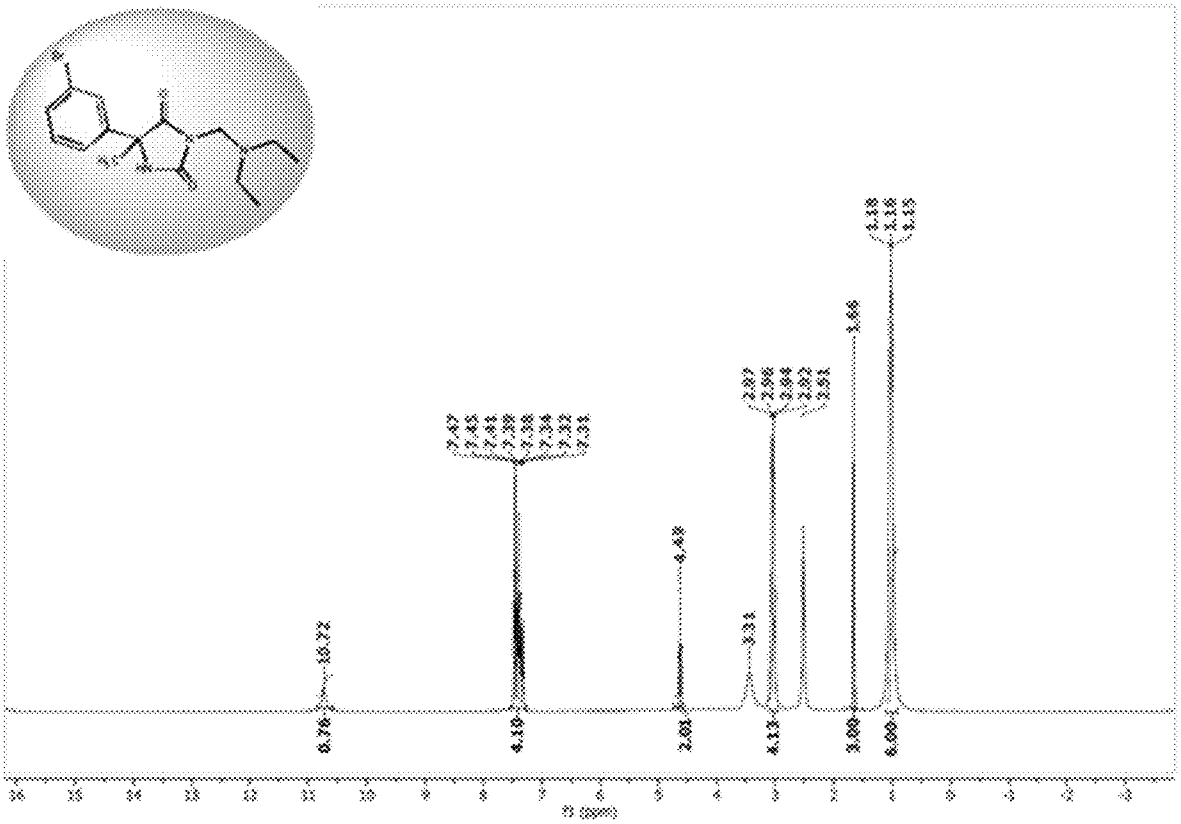
FIG. 1 shows a $^1H$ NMR analysis of the 5-(3-bromophenyl)-3-((diethylamino)methyl)-5-methylimidazolidine-2,4-dione compound.
Figure 2:
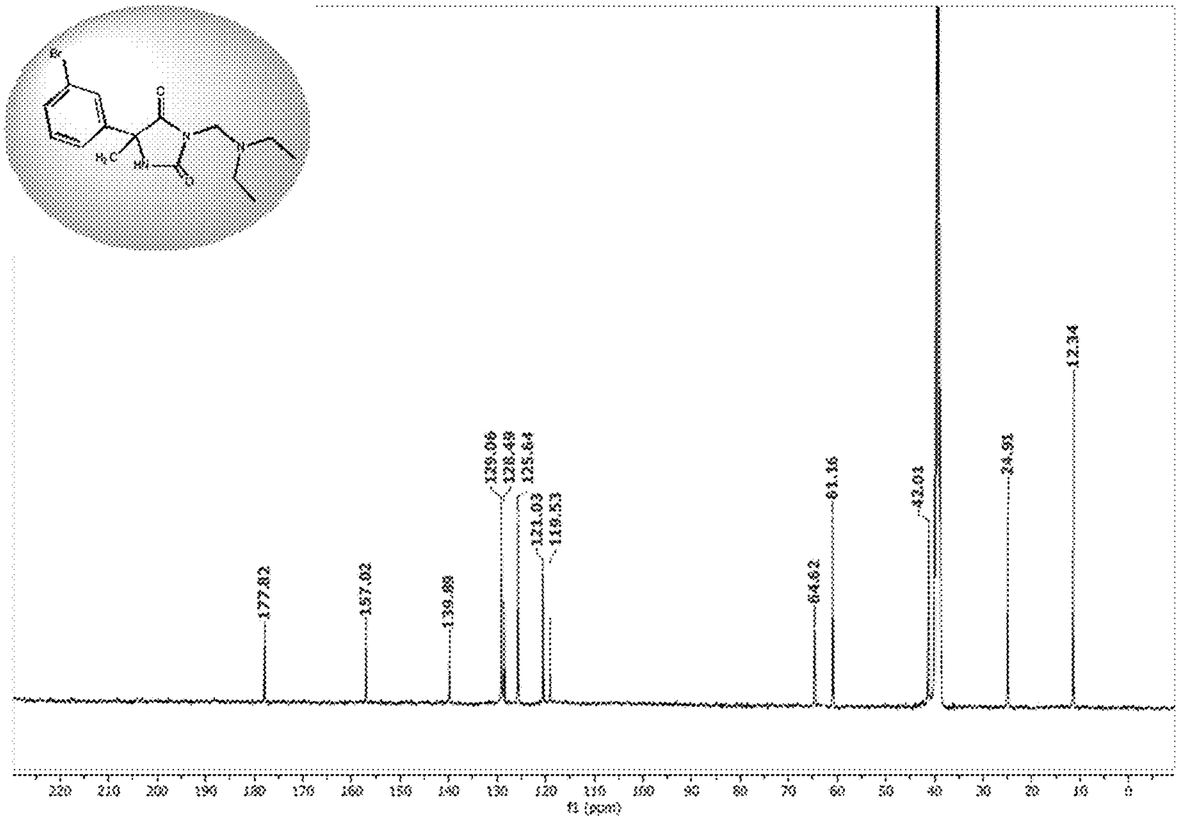
FIG. 2 shows a $^{13}C$ NMR analysis of the 5-(3-bromophenyl)-3-((diethylamino)methyl)-5-methylimidazolidine-2,4-dione compound.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as bacterial infection or Chronic Obstructive Pulmonary Disease (COPD).

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

A promising strategy to overcome the limitations of combination therapy is the design of hybrid antibacterial agents. This approach involves integrating two or more pharmacologically active structural units—each targeting distinct bacterial pathways into a single molecular framework through covalent linkages. Such hybrids not only minimize side effects but also enhance antibacterial efficacy by simultaneously engaging multiple mechanisms of action. Hybrid molecules are particularly valuable in combating bacterial resistance, as their multi-targeted activity reduces the likelihood of resistance development while improving binding affinity and potency compared to their parent drugs. By merging complementary pharmacological properties into a single entity, these hybrids represent novel drug leads with expanded therapeutic potential, offering a robust platform for next-generation antibiotic development.

The present subject matter relates to a novel heterocyclic compound, 5-(3-bromophenyl)-3-((diethylamino)methyl)-5-methylimidazolidine-2,4-dione (4). The compound can be synthesized via a one-pot three-component reaction of 5-(3-bromophenyl)-5-methylimidazolidine-2,4-dione (1), formaldehyde (2), and diethylamine (3) in ethanol. The compound (4) exhibited stronger antibacterial activity than the standard drug ciprofloxacin against *Bacillus cereus* and *Escherichia coli* at varying concentrations (10,000 ppm, 30,000 ppm, and 40,000 ppm).

The compound (4) can inhibit key inflammatory pathways associated with Chronic Obstructive Pulmonary Disease (COPD). Specifically, the 5-(3-bromophenyl)-3-((diethylamino)methyl)-5-methylimidazolidine-2,4-dione compound (4) showed notable inhibition of pro-inflammatory cytokines (e.g., TNF-α, IL-6) and reactive oxygen species (ROS)

production in lung epithelial cells, suggesting a dual-function profile as both an antibacterial and anti-COPD agent.

In an embodiment, the present subject matter relates to a 5-(3-bromophenyl)-3-((diethylamino)methyl)-5-methylimidazolidine-2,4-dione compound having the formula I:

I

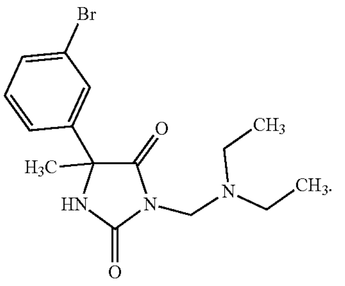

In certain embodiments, the 5-(3-bromophenyl)-3-((diethylamino)methyl)-5-methylimidazolidine-2,4-dione compound can be obtained as crystals. In further embodiments, the 5-(3-bromophenyl)-3-((diethylamino)methyl)-5-methylimidazolidine-2,4-dione compound can have a melting point of about 137° C. to about 139° C.

In another embodiment, the present subject matter relates to a pharmaceutically acceptable composition comprising a therapeutically effective amount of the 5-(3-bromophenyl)-3-((diethylamino)methyl)-5-methylimidazolidine-2,4-dione compound and a pharmaceutically acceptable carrier.

In this regard, the present subject matter is further directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises the present compound together with at least one pharmaceutically acceptable auxiliary.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to provide treatment for a bacterial infection and/or COPD. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for treatment of bacterial infections, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In a further embodiment, the present subject matter relates to a method of treating a bacterial infection in a patient comprising administering to a patient in need thereof a therapeutically effective amount of the 5-(3-bromophenyl)-3-((diethylamino)methyl)-5-methylimidazolidine-2,4-dione compound.

In certain embodiments in this regard, the bacterial infection can be caused by one or more bacteria.

In an embodiment, the bacteria infection can be caused by one or more gram positive bacteria. In this regard, non-limiting examples of the one or more gram positive bacterial strains causing the bacterial infection include *Bacillus cereus* and *Staphylococcus aureus*. In another embodiment, the bacterial infection can be caused by one or more gram negative bacteria. In this regard, non-limiting examples of the one or more gram-negative bacterial strains causing the bacterial infection include *Pseudomonas aeruginosa* and *Escherichia coli*.

In one more embodiment, the present subject matter relates to a method of making the 5-(3-bromophenyl)-3-((diethylamino)methyl)-5-methylimidazolidine-2,4-dione compound of claim 1, the method comprising: stirring 5-(3-bromophenyl)-5-methylimidazolidine-2,4-dione and formaldehyde in ethanol to form a first mixture; adding diethylamine to the first mixture to obtain a second mixture; stirring the second mixture with reflux; cooling the second mixture to form a solid; filtering the solid and recrystallizing from ethanol to obtain the 5-(3-bromophenyl)-3-((diethylamino)methyl)-5-methylimidazolidine-2,4-dione compound.

The present production methods can be further seen by referring to the following Scheme 1:

Scheme 1

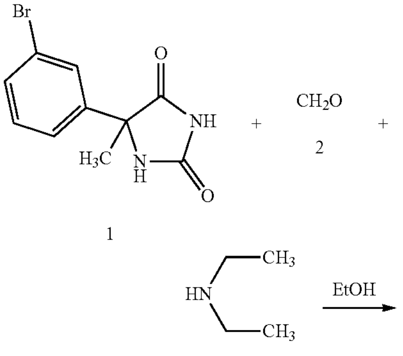

1

2

3

-continued

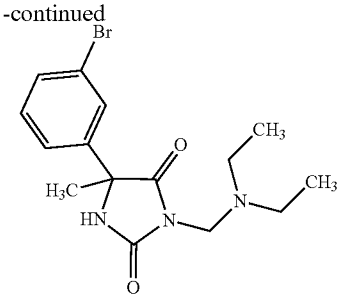

4

In an embodiment of the present production methods, the first mixture may be stirred with reflux.

In another embodiment of the present production methods, the first mixture may be stirred with reflux for 1 hour.

In a further embodiment of the present production methods, 60 mL of ethanol may be stirred with the 5-(3-bromophenyl)-5-methylimidazolidine-2,4-dione and formaldehyde.

In an embodiment of the present production methods, the 5-(3-bromophenyl)-5-methylimidazolidine-2,4-dione, formaldehyde, and diethylamine may be added in an about 1:2:1 molar ratio.

In an additional embodiment of the present production methods, the 5-(3-bromophenyl)-3-((diethylamino)methyl)-5-methylimidazolidine-2,4-dione compound can be obtained in an about 78% yield.

The following examples relate to various methods of manufacturing the specific compounds and application of the same, as described herein. All compound numbers expressed herein are with reference to the synthetic pathway figures shown above.

EXAMPLES

Example 1

Preparation of 5-(3-bromophenyl)-3-((diethylamino) methyl)-5-methylimidazolidine-2,4-dione (4)

A solution of 5-(3-bromophenyl)-5-methylimidazolidine-2,4-dione (1) (0.57 g, 0.003 mol) and formaldehyde (0.2 g, 0.007 mol) was stirred with refluxed in 60 mL ethanol for 1 hour, then diethylamine (0.22 g, 0.003 mol) was added and the reaction mixture was stirred with reflux for 3 hours. The reaction mixture was allowed to cool at room temperature, the separated solid was filtered off and recrystallized from ethanol to give the desired product 5-(3-bromophenyl)-3-((diethylamino)methyl)-5-methylimidazolidine-2,4-dione (4).

Characterization data for 5-(3-bromophenyl)-3-((diethylamino)methyl)-5-methylimidazolidine-2,4-dione (4):

Mp. 137-139° C. Yield=78%. FTIR (KBr, $cm^{-1}$) 3222 (NH), 3028 (CHarom.), 2962, 2857 (CHaliph.), 1719 and 1708 (C═O). $^{1}$H-NMR (DMSO-d6/$D_2O$, 400 MHz): 10.72 (br. NH), 7.47-7.31 (m, 4H, CHarom.), 4.49 (s, 2H, N—$CH_2$—N), 2.95 (q., J=8 Hz, 4H, 2$CH_2$), 1.66 (s, 3H, $CH_3$), 1.16 (t, J=8 Hz, 6H, 2$CH_3$); $^{13}$C NMR (100 MHz, DMSO-d6/$D_2O$): δ 177.82, 176.84, 157.02, 139.89, 129.06, 128.49, 125.64, 121.03, 119.53, 64.62, 61.16, 42.01, 24.91, 12.34; Analysis: calculated for $C_{15}H_{20}BrN_3O_2$ (354.24): C, 50.86; H, 5.69; N, 11.86%. Found: C, 50.98; H, 5.49; N, 11.63%.

Example 2

Antibacterial Activity

Antibacterial Testing Methods

Dimethyl sulfone ($DMSO_2$) was used to dissolve the constituent parts, and the same amounts was used in negative control experiments to make sure the solvent had no impact on bacterial growth or enzyme activity. The agar diffusion method (cup and plate method) was used to assess the inhibitory effect of compound 5-(3-Bromophenyl)-3-((diethylamino)methyl)-5-methylimidazolidine-2,4-dione (4) on the growth of a wide range of bacteria, including bacterial strains such as *Pseudomonas aeruginosa* and *Escherichia coli, Bacillus cereus* and *Staphylococcus aureus*. Using agar plates to measure the zone of inhibition at three distinct doses. The solvent control levels were 10 ppm, 30 ppm, and 50 ppm of methane sulfinylmethane. For twenty-four hours, each plate was incubated at 37±0.5° C. Using a millimeter scale, the compounds' zone of inhibition was determined.

5-(3-bromophenyl)-3-((diethylamino)methyl)-5-methylimidazolidine-2,4-dione 4 was examined to determine antibacterial effects against gram-positive bacteria, specifically *Bacillus cereus* and *Staphylococcus aureus* and gram-negative bacterial strains, namely *Pseudomonas aeruginosa* and *Escherichia coli* at concentration (A=10,000, B=30.000, C=40,000 ppm) by agar diffusion method. The results of the antibacterial test are shown in Table 1. Notably, compound 4 demonstrated excellent inhibition against *Bacillus cereus* and *Escherichia coli*, more than standard antibacterial drugs (ciprofloxacin) at all concentrations. Moreover, the compound showed a higher inhibition zone compared to ciprofloxacin at the concentration of 40,000 ppm against *Staphylococcus aureus*. However, the compound showed poor inhibitory effect against *Pseudomonas aeruginosa* at low concentration, while inhibition increased against *Staphylococcus aureus* by increasing the concentration.

TABLE 1

Antibacterial activity of 5-(3-bromophenyl)-3-((diethylamino)methyl)-5-methylimidazolidine-2,4-dione 4 by measuring inhibition zone (mm).

| | Gram positive | | | | | | Gram negative | | | | | |
|---|---|---|---|---|---|---|---|---|---|---|---|---|
| Type | *Bacillus Cereus* | | | *Staphylococcus aureus* | | | *Pseudomonas aeruginosa* | | | *Escherichia coli* | | |
| Comp. | A | B | C | A | B | C | A | B | C | A | B | C |
| 4 | 25 | 31 | 35 | 20 | 30 | 34 | 18 | 24 | 32 | 27 | 35 | 46 |
| Control | 0 | 0 | 0 | 0 | 0 | 0 | 0 | 0 | 0 | 0 | 0 | 0 |
| Cip. | 27 | 32 | 37 | 35 | 40 | 44 | 26 | 30 | 40 | 30 | 38 | 45 |

A = concentration of compound = 10,000 ppm.
B = concentration of compound = 30.000 ppm.
C = concentration of compound = 40,000 ppm.

It is to be understood that the 5-(3-Bromophenyl)-3-((diethylamino)methyl)-5-methylimidazolidine-2,4-dione compound, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating a bacterial infection in a patient comprising administering to a patient in need thereof a therapeutically effective amount of a 5-(3-bromophenyl)-3-((diethylamino)methyl)-5-methylimidazolidine-2,4-dione compound of formula 1 and a pharmaceutically acceptable carrier:

I

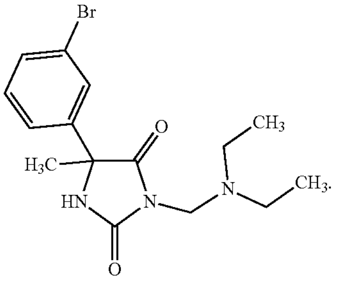

2. The method of treating the bacterial infection of claim 1, wherein the bacterial infection is caused by one or more bacteria.

3. The method of treating the bacterial infection of claim 2, wherein the bacterial infection is caused by at least one of a gram positive bacteria, a gram negative bacteria, and a combination thereof.

4. The method of treating the bacterial infection of claim 3, wherein the gram positive bacteria is selected from the group consisting of *Bacillus cereus, Staphylococcus aureus*, and a combination thereof.

5. The method of treating the bacterial infection of claim 3, wherein the gram negative bacteria is selected from the group consisting of *Pseudomonas aeruginosa, Escherichia coli*, and a combination thereof.

6. A method of treating chronic obstructive pulmonary disease (COPD) inhibition in a patient comprising administering to a patient in need thereof a therapeutically effective amount of a 5-(3-bromophenyl)-3-((diethylamino)methyl)-5-methylimidazolidine-2,4-dione compound of formula 1 and a pharmaceutically acceptable carrier:

I

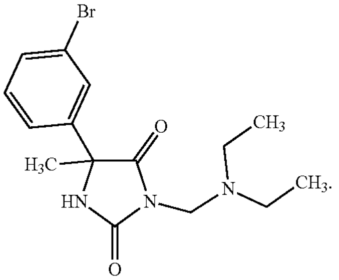

* * * * *